(12) United States Patent  (10) Patent No.: US 8,558,023 B2
Liu et al.  (45) Date of Patent: Oct. 15, 2013

(54) ENANTIOSELECTIVE PROCESS FOR CYCLOALKENYL β-SUBSTITUTED ALANINES

(75) Inventors: Zijun Liu, Suzhou (CN); Sanhui Lin, Suzhou (CN); Wenge Li, Plainsboro, NJ (US); Jingyang Zhu, Monmouth Junction, NJ (US); Xinjun Liu, Suzhou (CN); Xiaojuan Zhang, Suzhou (CN); Hui Lu, Suzhou (CN); Fei Xiong, Suzhou (CN); Zhongwei Tian, Suzhou (CN)

(73) Assignee: Chiral Quest, Inc., Monmouth Junction, NJ (US)

( * ) Notice: Subject to any disclaimer, the term of this patent is extended or adjusted under 35 U.S.C. 154(b) by 93 days.

(21) Appl. No.: 13/090,632

(22) Filed: Apr. 20, 2011

(65) Prior Publication Data

US 2011/0257408 A1    Oct. 20, 2011

Related U.S. Application Data

(60) Provisional application No. 61/326,187, filed on Apr. 20, 2010.

(51) Int. Cl.
C07C 229/28   (2006.01)
C07C 229/32   (2006.01)

(52) U.S. Cl.
USPC .............................................. 560/39; 560/41

(58) Field of Classification Search
None
See application file for complete search history.

(56) References Cited

U.S. PATENT DOCUMENTS

| 4,659,838 | A | 4/1987 | Lerch |
|---|---|---|---|
| 7,105,702 | B2 | 9/2006 | Zhang et al. |
| 2007/0021490 | A1 | 1/2007 | Gunjal et al. |
| 2009/0017509 | A1 | 1/2009 | Berk et al. |

FOREIGN PATENT DOCUMENTS

| DE | 3345355 A1 | 6/1985 |
|---|---|---|
| EP | 115345 A1 | 8/1984 |
| EP | 1354876 A1 | 10/2003 |
| EP | 1565485 A1 | 8/2005 |
| EP | 1688427 A1 | 8/2006 |
| GB | 2395195 A | 5/2004 |
| WO | 2004/046172 A1 | 6/2004 |
| WO | 2004/083237 A1 | 9/2004 |
| WO | 2007/079871 A1 | 7/2007 |
| WO | 2007/085933 A2 | 8/2007 |
| WO | 2009/098251 A1 | 8/2009 |

OTHER PUBLICATIONS

Pal et al Journal of the American Chemical Society (1956), 78,5116-18.*
Snow et al, Journal of Organic Chemistry (1968), 33(5), 1774-80.*

* cited by examiner

*Primary Examiner* — Kamal Saeed
(74) *Attorney, Agent, or Firm* — Fox Rothschild LLP; Peter J. Butch, III; Robert N. Henrie, II

(57) ABSTRACT

A process for preparing an enantiomerically enriched cycloalkene-substituted alanine compound having the structure:

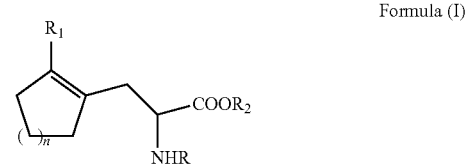

Formula (I)

by asymmetrically hydrogenating a dehydro amino acid compound having the structure:

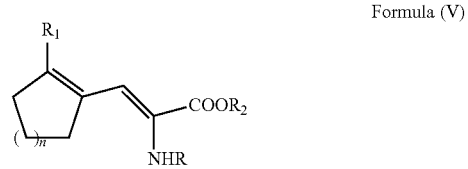

Formula (V)

in a suitable reaction media in the presence of a catalyst having a transition metal moiety complexed to a chiral phosphine ligand to prepare enantiomerically enriched cycloalkene substituted alanine compounds having the structure of Formula (IA) or (IB), which are key intermediates for the ACE inhibitors ramipril and perindolpril:

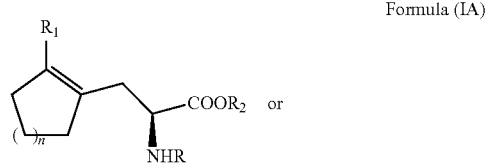

Formula (IA)

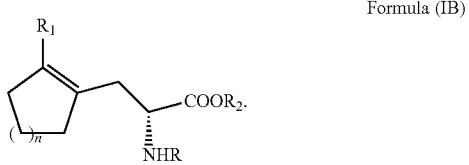

Formula (IB)

22 Claims, No Drawings

ENANTIOSELECTIVE PROCESS FOR CYCLOALKENYL β-SUBSTITUTED ALANINES

CROSS REFERENCE TO RELATED APPLICATIONS

This application claims priority to U.S. Provisional Application No. 61/326,187 filed Apr. 20, 2010, which is incorporated herein by reference in its entirety.

BACKGROUND OF THE INVENTION

The present invention relates to an enantioselective process for preparing optically pure β-cycloalkenyl-substituted alanines (Formula I, IA and IB), which could be easily converted to cyclic amino acids (Formula II) that are key intermediates for the ACE inhibitors ramipril (Formula III) and perindolpril (Formula IV).

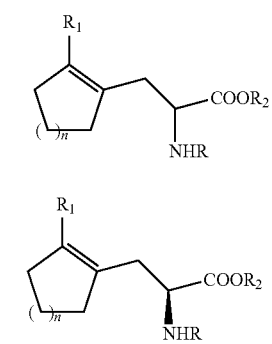

Cycloalkenyl Substituted Alanines

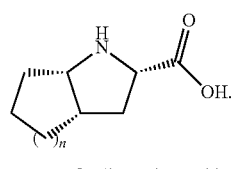

Cyclic Amino Acid

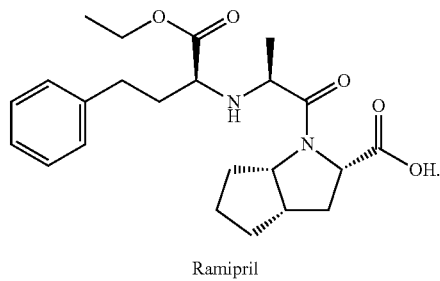

Ramipril

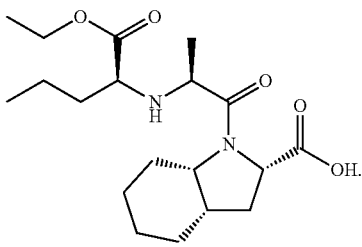

Perindopril

Ramipril [A. Kleemann, J. Engel, Pharmaceutical Substances, $4^{th}$ Edition, page 1785, Thieme Verlag Stuttgart, 2001] and perindolpril [EP 1565485, EP1688427] are ACE inhibitors which are frequently employed in the medical management of hypertension. One of the key intermediates is the cyclic amino acid of Formula II (n=1, 2). The five member ring amino acid with Formula II, wherein n is 1, is used for the preparation of Ramipril [WO 2009/098251, US 2009/0017509, WO 2007/079871]; while the six member ring amino acid with Formula II, wherein n is 2, is used for the preparation of perindolpril [EP 1354876, US 2007021490, WO 2004083237, WO2007085933].

The prior art for preparing the above mentioned amino acids employed such processes as chemical resolution [e.x. DE 3345355, EP 115345] or bio-transformation [e.x. US 2009/0017509]. However, these processes waste about half of the quantity of the precursor material and produce undesired isomers.

SUMMARY OF THE INVENTION

The present invention addresses the shortcomings of the prior art methodologies. The objective of this invention is to provide an alternative process for synthesizing cyclic amino acids that are useful intermediates of for Ramipril and Perindolpril. The present invention employs asymmetric hydrogenation to produce optically pure substituted alanines, which are easily converted to cyclic amino acids of interest. In contrast to the prior art chemical resolution processes, the presently claimed novel asymmetric hydrogenation procedure produces only one desired enantiomer with high yield. The presently claimed process is also advantageous from an economic and material utilization point of view.

In at least one aspect of the present invention, a process is provided for preparing an enantiomerically enriched substituted alanine compound or derivatives thereof having the structure:

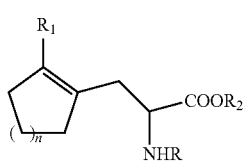

by hydrogenating a prochiral substrate compound having the structure:

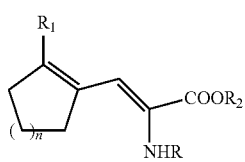

Formula (V)

in a reaction media in the presence of a transition metal precursor complexed to a chiral phosphine ligand wherein: n is 1, 2, 3, or 4, $R_1$ is independently selected from the group consisting of hydrogen, halogen, alkyl, alkoxy, aryloxy and —$COOR_4$, R is selected from hydrogen, alkyl, aryl, alkoxy, or aryloxy, and alkyl carboxy or aryl carboxy forming an amide linkage with the —NH to form —$NHCOR_4$, and $R_2$ is selected from hydrogen and alkyl, and $R_4$ is selected from alkyl and aryl groups.

In at least another aspect, the novel process of the present invention employs an (S) or (R) chiral phosphine ligand to hydrogenate the prochiral dehydro amino acid substrate compounds of Formula (V). In at least one embodiment of this aspect of the present invention, the chiral phosphine ligand catalyst has a formula M(L)(P*)X, wherein M is a transitional metal, preferably selected from the group consisting of Rh, Ru, and Ir; L is 1,5-cyclooctandiene or 2,5-norbornadiene; P* is a chiral phosphine compound, and X is a pharmaceutically suitable anion.

In a preferred embodiment for this aspect of the invention, chiral phosphine compounds employed are ScRp-DuanPhos, RcSp-DuanPhos, SSRR-TangPhos, BINAP, DuPhos and BPE. In a more preferred embodiment, the chiral phosphine catalyst is [Rh(COD)(ScRp-DuanPhos)]$BF_4$ or [Rh(COD)(RcSp-DuanPhos)]$BF_4$.

In at least another aspect of the present invention an unsaturated aldehyde having the structure:

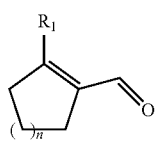

Formula (VI)

is converted to an azlactone compound having the structure:

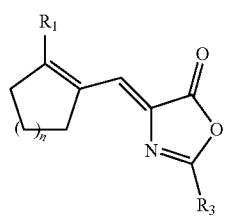

Formula (VIII)

under an Erlenmeyer-Plochl reaction conditions. In a preferred embodiment of this aspect of the invention, n=1, 2, 3 or 4; $R_1$ is hydrogen, chloro, bromo, phenoxy, alkoxy or naphthoxy, and $R_3$ is alkyl or aryl.

In at least another aspect of the present invention the novel process employs a step of converting the azlactone of Formula (VIII) to a substituted prochiral dehydro amino acid substrate compound having the structure

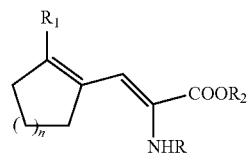

Formula (V)

wherein n, R, and $R_1$ are as stated above, and $R_2$ is hydrogen, methyl or ethyl. In a more preferred embodiment of this aspect of the invention, the step of converting the azlactone of Formula (VIII) to the dehydro amino acid of Formula (V) is accomplished by an alcoholysis reaction step.

In accordance with another aspect of the present invention the prochiral dehydro amino acid of Formula (V) is asymatrically hydrogenated to prepare enantiomerically pure cycloalkyene substituted alanine compounds of Formula (IA) or (IB).

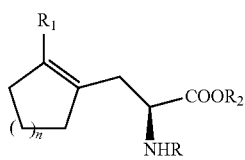

Formula (IA)

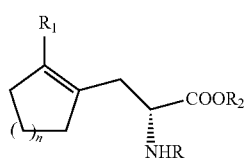

Formula (IB)

In a more preferred embodiment, the compounds of Formula (IA) and (IB) are enriched, pure, or most preferably enantiomoreically enriched and pure as defined herein.

In another aspect of the present invention the compound having a structure of Formula (IA) undergoes a hydrolysis step to prepare compounds having the structure

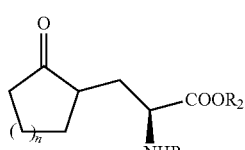

Formula (IX)

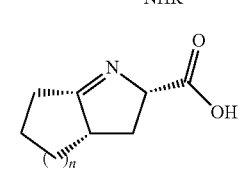

Formula (X)

wherein n, R and $R_2$ are as stated above.

In another aspect of the present invention, compounds of Formula (IX) and (X) undergo a step of catalytic hydrogenatation to prepare a cyclic amino acid having the structure of Formula (II):

Formula (II)

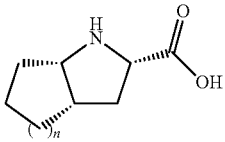

In this aspect of the invention a metal-based hetro or homo catalyst is selected from the group consisting of Pt, Pd, Rh with or without a ligand.

In another aspect of the present invention, novel compounds are provided having the general structure Formula (VI)

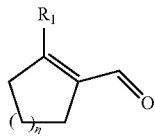

n is 1, 2, 3, or 4; $R_1$ is $R_1$ is hydrogen, a halogen, an alkyl, an alkoxy, an aryl, an aryloxy, an alkyl carboxy, an aryl carboxy and a cycloalkyl, and preferably alkoxy or aryloxy, with the proviso that if n is 1, $R_1$ is not methoxy and if n is 2, $R_1$ is not phenoxy. In a more preferred embodiment of this aspect of the invention $R_1$ can be $C_2$-$C_{10}$ alkoxy, phenoxy or naphthoxy.

In another aspect of the present invention, new compounds are provided having the structure:

Formula (VIII)

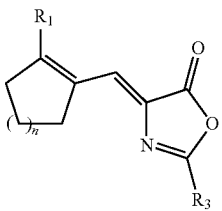

wherein n is 1, 2, 3, or 4; $R_1$ and $R_3$ are independently selected from a group consisting of halogen, alkyl, alkoxy, aryl, aryloxy, alkyl carboxy, aryl carboxy and cycloalkyl. In yet a preferred embodiment of this aspect of the invention, $R_1$ is Cl, Br, phenoxy, alkoxy and naphthoxy, and $R_3$ is an aryl, or an alkyl.

In another aspect of the present invention, pure enantiomerically enriched compounds are provided having the structure:

Formula (IA)

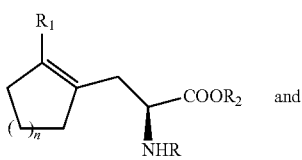 and

Formula (IB)

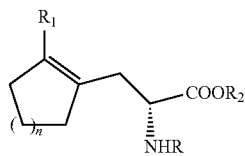

wherein n, $R_1$, and $R_2$ are as above. In a preferred embodiment $R_1$ is Cl, Br, phenoxy, alkoxy and naphthoxy, and $R_3$ is an aryl, or an alkyl, and R is an alkyl, aryl or —$COR_4$. When R is $COR_4$, NHR is an amide group formed between the —NH and $COR_4$ to construct a —$NHCOR_4$.

Accordingly, at least one aspect of the present invention provides an enantioselective process for producing a substituted alanine compound having the structure:

Formula (IA)

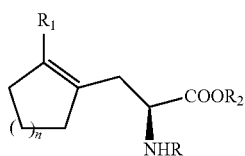

Cycloalkenyl (s)β—Substituted Alanine wherein R, $R_1$ and $R_2$ are independently a hydrogen, or alkoxy, or aryloxy, or an alkyl group, or halogen, or alkyl carboxy, or aryl carboxy. In particular, R is acetyl or benzoyl and $R_1$ is halogen or aryloxy. More particularly $R_1$ is chloro, bromo, or phenoxy and $R_2$ is a $C_{1-4}$ alkyl group. Even more particularly, $R_2$ is methyl or ethyl.

The novel enantioselective process employs at least one step of asymmetrically hydrogenating a compound having the structure:

Formula (V)

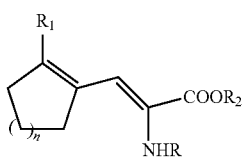

in the presence of a chiral phosphine transition metal catalyst.

In one embodiment of this aspect of the present invention, the novel process for producing a substituted alanine employs enantioselective catalysts which are phosphine compounds represented by the Formula M(L)(P*)X, wherein M represents Rh, Ru, and Ir; L represents 1,5-cyclooctandiene or 2,5-norbornadiene; P* represents a chiral mono- and bidentate phosphine compound, and X represents a tetrahaloborate. In another embodiment of this aspect of the invention, P* is selected from the group consisting of ScRp-DuanPhos, RcSp-DuanPhos, SSRR-TangPhos, R-BINAP, S-BINAP DuPhos and BPE.

In one aspect of the present invention, the compounds of Formula (V) are prepared by reacting the unsaturated aldehyde of Formula (VI) with the substituted glycine of Formula (VII) under Erlenmeyer-Plochl reaction conditions via an intermediate of Formula VIII, wherein R, $R_1$, $R_2$ and $R_3$ are independently a hydrogen, or alkoxy, or aryloxy, or an alkyl group, halogen, alkyl carboxy, or aryl carboxy. Particularly, R is acetyl or benzoyl and $R_1$ is halogen or aryloxy. More particularly $R_1$ is chloro, bromo, or phenoxy and $R_2$ and $R_3$ are $C_{1-4}$ alkyl or aryl groups. More particularly, $R_2$ is methyl or ethyl and $R_3$ is methyl or phenyl.

In another aspect of the present invention, the compounds of Formula (V) are prepared by alcoholysis of the compounds of Formula (VIII):

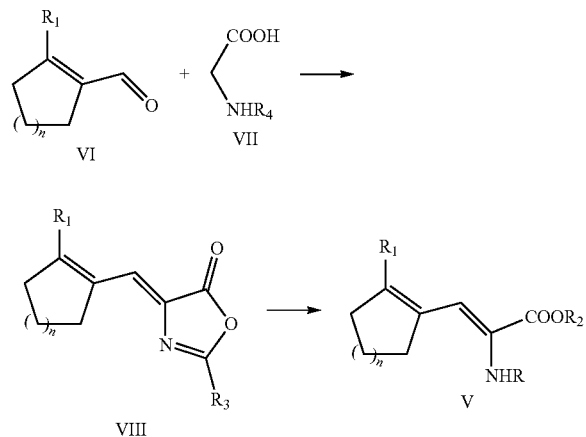

In another aspect of the present invention, compounds having the structure of Formula (VIB), are prepared by reacting a compound having the structure of Formula (VIA) with phenol in the presence of base, which could be sodium hydroxide, potassium hydroxide, sodium carbonate, potassium carbonate or triethyl amine. Potassium carbonate and triethyl amine are preferred.

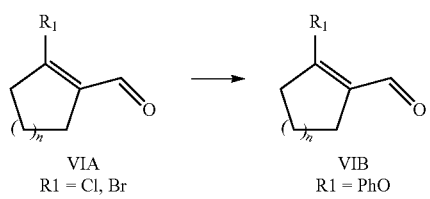

In another aspect of the present invention, compounds having the structure of Formula (I), (V), (VIB) and (VIII) are disclosed. Accordingly, Formula (IA) is

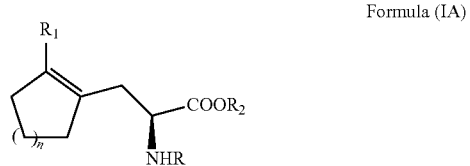

Formula (IA)

wherein R is an alkyl group or —$COR_4$ forming an amide linkage between the —NH to construct a —$NHCOR_4$; $R_1$ is an alkyl, alkoxy or aryloxy group or $COOR_4$, and $R_2$ an alkyl group wherein $R_4$ is an alkyl or aryl group. In particular, NHR is an acetyl or benzoyl amide group and $R_1$ is aryloxy. More particularly $R_1$ is phenoxy. $R_2$ is preferably a $C_{1-4}$ alkyl group and more particularly, $R_2$ is methyl or ethyl.

Formula (V) is

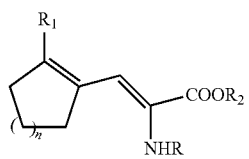

V wherein R, $R_1$ and $R_2$ are the same as described above in Formula (I).

Formula (VIB) is

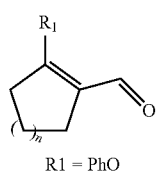

VIB

R1 = PhO wherein $R_1$ phenoxy group.

Formula (VIII) is

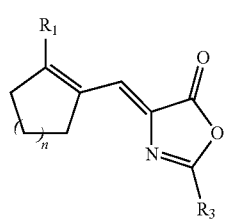

VIII wherein $R_1$ is the same as described above in Formula I and $R_3$ is alkyl or aryl. Particularly $R_3$ is methyl or phenyl.

DETAILED DESCRIPTION OF THE PREFERRED EMBODIMENTS

As employed above and throughout the disclosure, the following terms, unless otherwise indicated, shall be understood to have the following meanings:

The term "Alkyl" refers to the radical of saturated aliphatic groups, including straight-chain alkyl groups and branched-chain alkyl groups. The term "cycloalkyl" refers to a non-aromatic mono or multicyclic ring system of about 3 to 7 carbon atoms. Examples of cycloalkyl groups include cyclopropyl, cyclobutyl, cyclopentyl, cyclohexyl and the like.

The term "alkoxy" as used herein refers to an alkyl group, as defined above, having an oxygen radical attached thereto. Representative alkoxy groups include methoxy, ethoxy, propoxy, t-butoxy, benzyloxy and the like.

The term "alkylcarboxy" as used herein refers to a —$COR_4$ group, wherein $R_4$ is an alkyl group.

The term "aryl" refers to any functional group or substituent derived from a simple aromatic ring, be it phenyl, thienyl, indolyl, etc.

The term "arylcarboxy" as used herein refers to a —$COR_4$ group, wherein $R_4$ is an aryl group, capable of forming an amide linkage.

The term "enantiomerically enriched compound" means optically active compounds with an enantiomeric excess (ee) of greater than 20%. The term "enantiomerically pure compound" means optically active compounds with an ee of greater than 99%. The term "enantiomerically enriched and essentially pure compound" means optically active compound with an ee of above 95% but less than 99%.

The term "halogen" refers to chlorine, bromine, fluorine or iodine. In more preferred embodiments, the halogen is selected from chlorine and bromine. The term "chiral phosphine transition metal catalyst" refers to catalyst compounds such as those described in U.S. Pat. No. 7,105,702, the teachings of which are incorporated herein by its entirety. The preferred phosphine compounds have the formula M(L)(P*)X, wherein M represents Rh, Ru, and Jr or a transitional metal moiety, salt or complexes including but not limited to (Rh(COD)X)$_2$; (Rh(COD)$_2$)X; Rh(acac)(CO)$_2$; Rh(ethylene)$_2$(acac); (Rh(ethylene)$_2$X)$_2$; RhCl(PPh$_3$)$_3$; Rh(CO)$_2$Cl$_2$; RuHX(L)$_2$(diphosphine), RuX$_2$(L)$_2$ (diphosphine), Ru(arene)X$_2$(diphosphine), Ru(aryl group)X$_2$; Ru(RCOO)$_2$(diphosphine); Ru(aryl group)X$_2$ (PPh$_3$)$_3$; Ru(COD)(COT); Ru(COD)(COT)X; Ru(COD)$_n$; Ru(arylgroup)X$_2$(diphosphine); RuCl$_2$(COD); (Ru(COD)$_2$)X; RuX$_2$ (diphosphine); Ru(ArH)Cl$_2$; Ru(COD)(methallyl)$_2$ and X is an anion; L represents 1,3,5-cyclooctatriene (COT), 1,5-cyclooctandiene (COD) or 2,5-norbornadiene; P* represents chiral mono- and bidentate phosphine compounds, such as, ScRp-DuanPhos, RcSp-DuanPhos, SSRR-TangPhos, R-BINAP, S-BIANP, (S,S)-DuPhos, (R,R)-DuPhos and (R,R)-BPE as well the enantiomer (SS)-BPE; wherein X is an anion.

A new process for preparing cyclic amino acids (Formula II) is elucidated in Scheme 1:

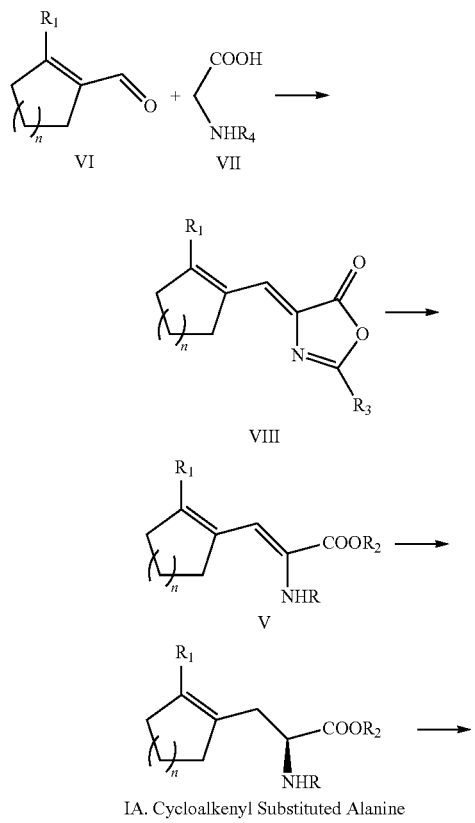

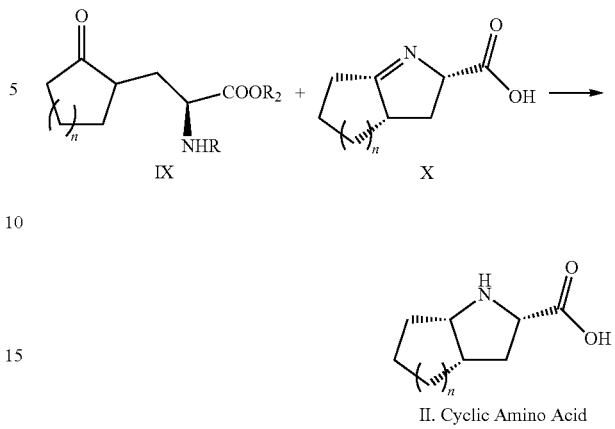

At least one aspect of the present invention requires that the final enantiomerically enriched compound to have an ee in the range of, for example, about 20% to about 99%. In yet another embodiment the compound may have an ee in the range of about 35% to 99%. In a preferred embodiment, the final compound would have an ee in the range of from about 40% to about 99%. In a more preferred embodiment, the final compound would have an ee in the range of about 45% to about 99% and in the most preferred embodiment, the enantiomerically enriched and essentially pure compound would have an ee greater than 95%. In one embodiment the enantiomerically enriched and essentially pure compound with the structure of Formula (IA) or (IB) is obtained with 97% ee; in another embodiment the enantiomerically pure compound with the structure of Formula (IA) or (IB) is obtained with 99% ee.

In particular, cyclic amino acids II are prepared in a process including the following steps:

(1) Formation of unsaturated aldehyde (VIB) by replacing the chloro or bromo in (VIA) with phenol, hydroquinone, hydroxy naphthalene or other substituted phenols in the presence of base.

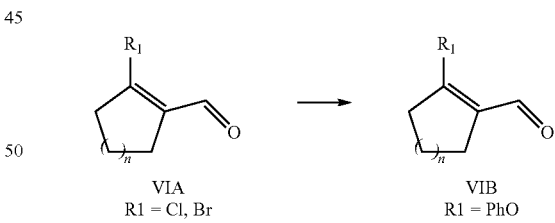

(2) Azlactone compound (VIII) formation under Erlenmeyer-Plochl reaction conditions.

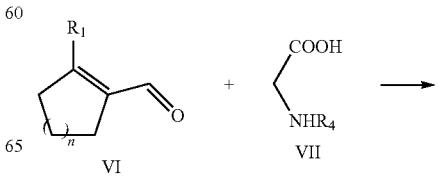

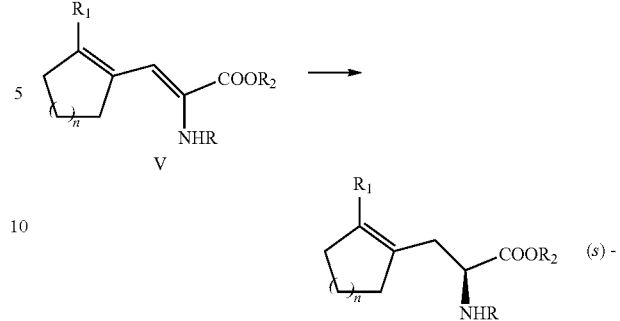

VIII

In one embodiment, the compound of Formula (VIII) is prepared via Erlenmeyer-Plochl type reaction of compound of Formula (VI), wherein n is 1, $R_1$ is phenoxy and $R_3$ is phenyl. In another embodiment of Formula VIII, $R_1$ is chloro and $R_3$ is phenyl.

(3) Preparation of the substituted dehydroamino acids Formula (V) via alcoholysis.

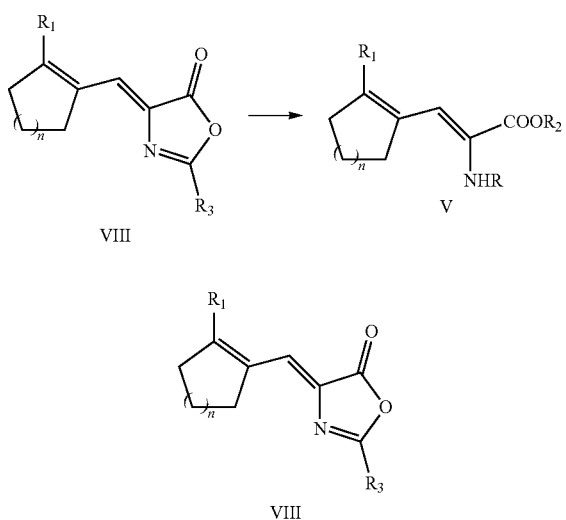

wherein $R_1$ and $R_3$ are independently halogen, phenoxy, phenyl and methyl. Specific embodiments are disclosed in Table I:

TABLE I

| Entry | $R_1$ | $R_3$    | n      |
|-------|-------|----------|--------|
| 1     | Cl    | Ph or Me | 1 or 2 |
| 2     | Br    | Ph or Me | 1 or 2 |
| 3     | PhO   | Ph or Me | 1 or 2 |

In one embodiment, the compound of Formula (V) is prepared by alcoholysis in hot methanol with a catalytic amount of base, such as sodium methoxide, wherein n is 1 and $R_1$ is phenoxy.

(4) Enantioselective preparation of substituted alanine. Compounds of Formula I are prepared via asymmetric hydrogenation of prochiral substrates (V).

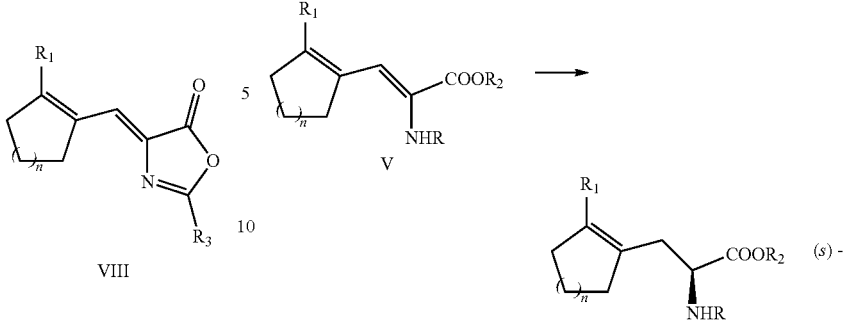

IA. Cycloalkenyl Substituted Alanine

The process of converting the compounds (V) to (I) is achieved by using a chiral phosphine-transition metal catalyst in the presence of hydrogen, such as those described in U.S. Pat. No. 7,105,702, the teachings of which are incorporated herein by its entirety.

The preferred phosphine compounds have the formula M(L)(P*)X, wherein M represents Rh, Ru, Ir; L represents 1,5-cyclooctandiene or 2,5-norbornadiene; P* represents chiral phosphine compounds, such as, ScRp-DuanPhos, RcSp-DuanPhos, SSRR-TangPhos, BINAP, DuPhos and BPE; X represents $BF_4$, $B(Ar)_4$ wherein Ar is fluorophenyl or 3,5-di-trifluoromethyl-1-phenyl, $ClO_4$, $SbF_6$, $PF_6$, $CF_3SO_3$, RCOO or a mixture thereof.

In a preferred embodiment M is Rh, Ru, or Ir; L represents 1,5-cyclooctandiene or 2,5-norbornadiene; P* represents ScRp-DuanPhos or RcSp-DuanPhos and X is tetrafluoroborate.

In at least one embodiment of this step, the hydrogen pressure can range from about 1 to about 50 bar, preferably in the ranges of about 1 bar to about 30 bar, and most preferably in the range of about 5 to about 10 bar.

The reaction media for this transformation is selected from dichloromethane, methanol, tetrahydrofuran, toluene, ethyl acetate and combinations thereof. In particular, dichloromethane, methanol and tetrahydrofuran are more suitable solvents while methanol is the most suitable solvent. The suitable reaction temperature for converting compounds of Formula (V) to compounds of Formula I can range from about 10 to about 50° C., and preferably in range of about 20 to about 30° C.

In accordance with the present invention it has turned out that both enantiomers of compounds of Formula I can be achieved by using chiral ligands, of which both enantiomers are available. In one embodiment of this aspect, a compound was produced with an (S)-configuration using [Rh(COD)(ScRp-DuanPhos)]$BF_4$ as the catalyst; while it was produced as an (R)-configuration using [Rh(COD)(RcSp-DuanPhos)]$BF_4$ as the catalyst.

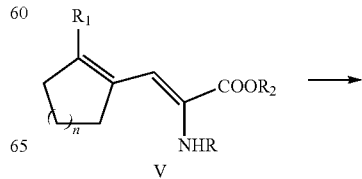

V

-continued

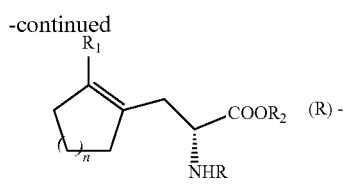

IB. Cycloalkenyl Substituted Alanine (5) Hydrolysis of substituted alanine.

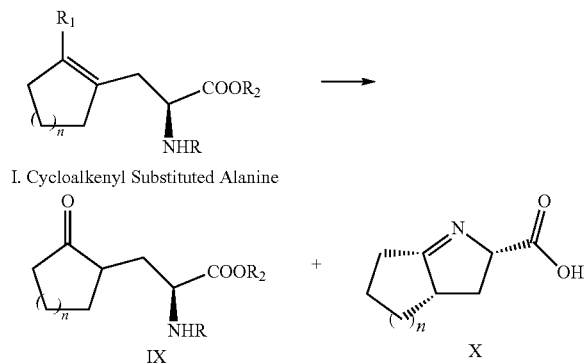

I. Cycloalkenyl Substituted Alanine

IX

X

This step of the reaction may be carried out in a hot acidic solution, such as hydrochloric acid solution and provides compounds of Formula (IX) or (X), or a mixture of compounds of formula (IX) and (X), or salts of compounds of Formula (IX) and (X), or a mixture of salts of compounds of Formula (IX) and (X). In the alternative, this step can be performed in the presence of concentrated sulfuric acid at lower temperatures to provide compound of Formula (IX), which can be further hydrolyzed to unprotected compounds of Formula (IX) and (X) as a mixture. In a preferred embodiment, the compound (I) having chloro as $R_1$, PhCO as R and methyl as $R_2$ can be hydrolyzed in the presence of concentrated sulfuric acid to compound Formula (IX) in which R is PhCO and $R_2$ is methyl.

(6) Preparation of the cyclic amino acids (II) by catalytic hydrogenation.

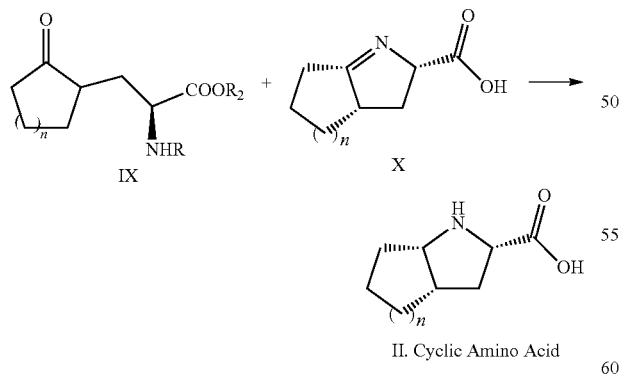

IX

X

II. Cyclic Amino Acid

In at least one embodiment of the present invention, the transformation of a mixture of salts of compounds (IX) and (X) depicted above was obtained with a metal-based heterogeneous catalyst or a homogeneous catalyst. These catalysts can be Pd on carbon, Pt on carbon, or ruthenium, rhodium and Iridium, with or without ligand.

In at least another embodiment of the present invention, this step can be carried out in a polar solvent such as water, methanol, ethanol, acetic acid or mixtures thereof, under a pressure of hydrogen between 5 and 15 bar, at a elevated temperature between 20 and 80° C. More preferably the step is carried out at 40° C. in acetic acid.

EXAMPLES

Example 1

Preparation of 2-chloro-1-formyl-1-cyclopentene (VIA)

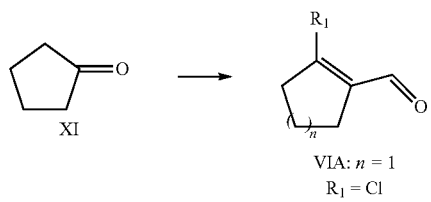

XI

VIA: $n = 1$
$R_1 = Cl$

To a three-necked flask fitted with a stirrer, thermometer, reflux condenser, additional funnel, nitrogen inlet, and calcium chloride drying tube were added dimethylformamide (71.8 g, 0.9 mol) and 1,2-dichloroethane (150 mL). The resulting mixture was stirred under nitrogen and cooled to 5° C. with an external ice bath. Phosphorus oxychloride was added during approximately 1 hour through an additional funnel while the temperature of the stirred reaction mixture being maintained below 10° C. The mixture was then allowed to warm to room temperature. A solution of cyclopentanone (55.5 g, 0.66 mol) in 1,2-dichloroethane (100 mL) was added at such a rate that the temperature did not rise above 35° C. When the addition was completed, the mixture was heated at 55-60° C. for 3 hours. The reaction mixture was then cooled to below 35° C., and a solution of sodium acetate (240 g) in water (560 mL) was cautiously added through an additional funnel. The organic layer was separated and washed with saturated brine twice and water once. The combined organics were dried over anhydrous sodium sulfate. The solvent was removed under reduced pressure providing 56 g product as oil, which was used for the next step without further purification.

$^1$H NMR (CDCl$_3$, δ): 10.00 (S, 1H), 2.82 (m, 2H), 2.59 (m, 2H), 2.01 (m, 2H).

Example 2

Preparation of 2-phenoxy-1-formyl-1-cyclopentene (VIB)

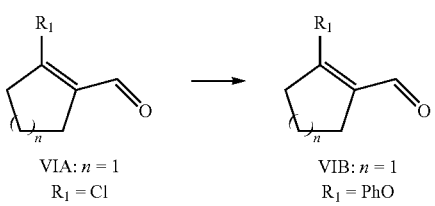

VIA: $n = 1$
$R_1 = Cl$

VIB: $n = 1$
$R_1 = PhO$

To a solution of residue (100 g, 0.77 mol) obtained in example 1 in acetone (400 mL), phenol (79.3 g, 0.84 mol) and K$_2$CO$_3$ (126.8 g, 0.92 mol) were added. The mixture was stirred under nitrogen for 12 hours at room temperature and monitored by TLC (petroleum ether/ethyl acetate=10:1). After the reaction completed, the solvent was removed on a rotary evaporator, and water (300 mL) was added. The mixture was extracted with EtOAc (2×100 mL). The organic layer was washed with aqueous sodium carbonate (2×50 mL) and water (50 mL). After dried over sodium sulfate, the solvent was removed and 2-phenoxy-1-formyl-1-cyclopentene was obtained (155 g, contains some phenol), which was used directly in the next step.

Example 3

Preparation of 4-((2-phenoxycyclopent-1-enyl)methylene-2-phenyloxzol-5(4H)-one (VIII)

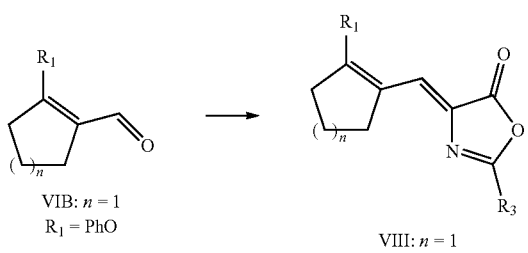

VIB: $n = 1$
R$_1$ = PhO

VIII: $n = 1$
R$_1$ = PhO
R3 = Ph

A mixture of 2-phenoxy-1-formyl-1-cyclopentene (150 g, obtained in example 2), acetic anhydride (196 g, 1.92 mol), sodium acetate (40 g, 0.48 mol) and benzoylglycine (125.7 g, 0.7 mol) was heated to 105-110° C. for about 1.5 h under nitrogen. The reaction was monitored by TLC (petroleum ether/ethyl acetate=15:1). After the reaction was completed, the mixture was cooled to 0° C., and then filtered. The cake was washed with methanol (2×150 mL) at room temperature. A brown to orange solid was obtained and dried in vacuum to afford 137 g product in 64.7% yield.

$^1$H NMR (CDCl$_3$, δ): 8.10-8.06 (m, 2H), 7.73-7.46 (m, 4H), 7.38-7.34 (m, 2H), 7.19-7.16 (m, 1H), 7.04-7.02 (m, 2H), 3.13 (t, 2H, J=7.2), 2.46 (t, 2H, J=7.6), 2.10-2.00 (m, 2H).

Example 4

Preparation of 4-((2-chlorocyclopent-1-enyl)methylene)-2-phenyloxzol-5(4H)-one (VIIIA)

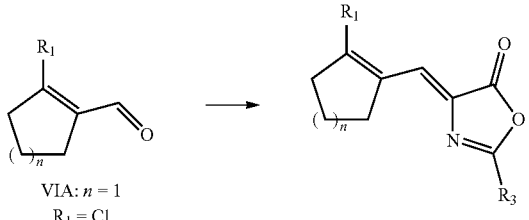

VIA: $n = 1$
R$_1$ = Cl

VIIIA: $n = 1$
R$_1$ = Cl
R3 = Ph

A mixture of 2-chloro-1-formyl-1-cyclopentene (105 g), acetic anhydride (196 g, 1.92 mol), sodium acetate (40 g, 0.48 mol) and benzoylglycine (125.7 g, 0.7 mol) was heated to 105-110° C. for about 1.5 h under nitrogen. The reaction was monitored by TLC. After the reaction was completed, the mixture was cooled to 0° C., and then filtered. The cake was washed with methanol twice (2×150 mL) at room temperature. A brown to orange solid was obtained and dried in vacuum to afford 187 g product in 85.1% yield.

$^1$H NMR (CDCl$_3$, δ): 8.01-7.99 (m, 2H), 7.50-7.40 (m, 3H), 7.20 (S, 1H), 3.10-3.05 (m, 2H), 2.70-2.68 (m, 2H), 2.10-2.00 (m, 2H).

Example 5

Preparation of (Z)-methyl-2-benzamido-3-(2-phenoxycyclopent-1-enyl)acrylate (V)

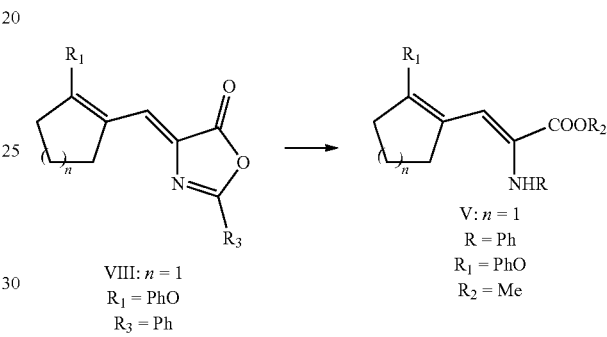

VIII: $n = 1$
R$_1$ = PhO
R$_3$ = Ph

V: $n = 1$
R = Ph
R$_1$ = PhO
R$_2$ = Me

To the slurry of compound (VIII) (n=1, R$_1$=PhO, R$_3$=Ph) (137 g, 0.41 mol) in methanol (400 mL), sodium methoxide (1.2 g, 0.015 mol) was added at room temperature. The mixture was refluxed for 0.5 h. After being cooled to 0° C., the mixture was filtered. The solid was washed with MTBE (200 mL). The filtrate was concentrated to one third volume to afford gray solid which was dried in vacuum to afford 140 g product in 93% yield.

$^1$H NMR (CDCl$_3$, δ): 7.87-7.85 (m, 2H), 7.70 (br, 1H), 7.56-7.52 (m, 1H), 7.48-7.44 (m, 3H), 7.34-7.30 (m, 2H), 7.15-7.11 (m, 1H), 7.02-6.99 (m, 2H), 3.78 (s, 3H), 2.65 (t, 2H, J=7.2), 2.35 (t, 2H, J=7.6), 1.92-1.84 (m, 2H).

Example 6

Preparation of (Z)-methyl-2-benzamido-3-(2-chlorocyclopent-1-enyl)acrylate (VA)

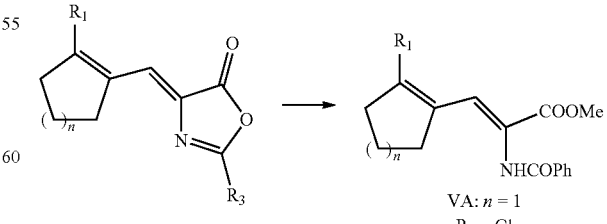

VIIIA: $n = 1$
R$_1$ = Cl
R3 = Ph

VA: $n = 1$
R$_1$ = Cl

To a slurry of compound (VIIIA) (n=1, $R_1$=Cl, $R_3$=Ph) (187 g, 0.605 mol) in methanol (600 mL) was added sodium methoxide (1.8 g, 0.022 mol) at room temperature. The mixture was refluxed for 0.5 h. After being cooled to 0° C., the mixture was filtered. The solid was washed with MTBE (300 mL). The filtrate was concentrated to one third volume to afford gray solid which was dried in vacuum to afford 177 g product in 95% yield.

$^1$H NMR (CDCl$_3$, δ): 7.87-7.84 (m, 2H), 7.60-7.50 (m, 5H), 3.83 (s, 3H), 2.65 (t, 4H, J=7.6), 1.95-1.88 (m, 2H).

Example 7

Preparation of (S)-methyl-2-benzamido-3-(2-phenoxycyclopent-1-enyl)propanoate (I)

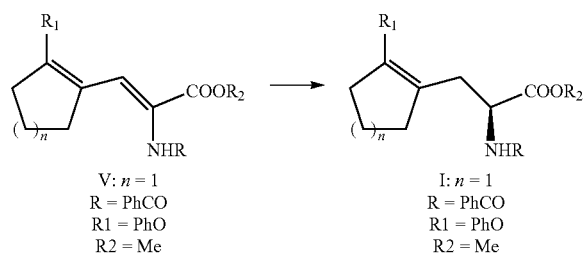

V: n = 1
R = PhCO
R1 = PhO
R2 = Me

I: n = 1
R = PhCO
R1 = PhO
R2 = Me

To a 2-L autoclave, a slurry of compound (V) (n=1, R=Ph, $R_1$=PhO, $R_2$=Me) (100 g, 0.27 mol) in methanol (900 mL) was charged and bubbled with nitrogen for 30 minutes. Then [Rh(COD)(ScRp-DuanPhos)]BF$_4$ (135 mg, 0.2 mmol) was added under nitrogen. The autoclave was then charged hydrogen to 10 bar and stirred at room temperature overnight. The reaction was monitored with HPLC. After the reaction completed, pressure of the hydrogenator was released, and the solution was concentrated to provide the product as oil (100 g). The ee was >99% which was determined by HPLC using Chiralpak AD-H column.

$^1$H NMR (CDCl$_3$, δ): 7.80-7.79 (m, 2H), 7.53-7.49 (m, 1H), 7.45-7.41 (m, 2H), 7.26-7.20 (m, 2H), 7.03-6.99 (m, 1H), 6.88-6.85 (m, 2H), 6.83 (br, 1H), 4.87-4.82 (m, 1H), 3.73 (s, 3H), 2.78-2.64 (m, 2H), 2.51-2.42 (m, 1H), 2.36-2.30 (m, 3H), 1.95-1.88 (m, 2H).

Example 8

Preparation of (S)-methyl-2-benzamido-3-(2-chlorocyclopent-1-enyl)propanoate (IA)

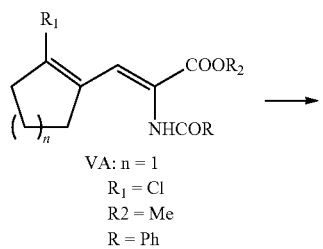

VA: n = 1
R1 = Cl
R2 = Me
R = Ph

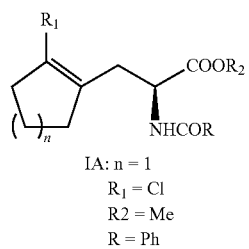

IA: n = 1
R1 = Cl
R2 = Me
R = Ph

To a 2-L autoclave, a slurry of compound VA (n=1, R=Ph, $R_1$=Cl, $R_2$=Me) (76 g, 0.25 mol) in methanol (700 mL) was charged and bubbled with nitrogen for 30 minutes. Then [Rh(COD)(ScRp-DuanPhos)]BF$_4$ (17 mg, 0.025 mmol) was added under nitrogen. The autoclave was then charged hydrogen to 10 bar and stirred at room temperature overnight. The reaction was monitored with HPLC. After the reaction completed, pressure was released, and the solution was concentrated to provide the product as oil (77 g). The ee was >99% which was determined by HPLC using Chiralpak AD-H column.

$^1$H NMR (CDCl$_3$, δ): 7.80-7.77 (m, 2H), 7.54-7.49 (m, 3H), 6.61 (br, 1H), 4.94-4.88 (m, 1H), 3.78 (s, 3H), 2.79-2.76 (m, 2H), 2.55-2.45 (m, 3H), 2.37-2.30 (m, 1H), 1.96-1.88 (m, 2H).

Example 9

Hydrolysis of (I) into a mixture of (2S)-2-amino-3-(2-oxocyclopentyl)propanoic acid (IX) and (2S)-2,3,3a,4,5,6-hexahydrocyclopenta[b]pyrrole-2-carboxylic acid (X)

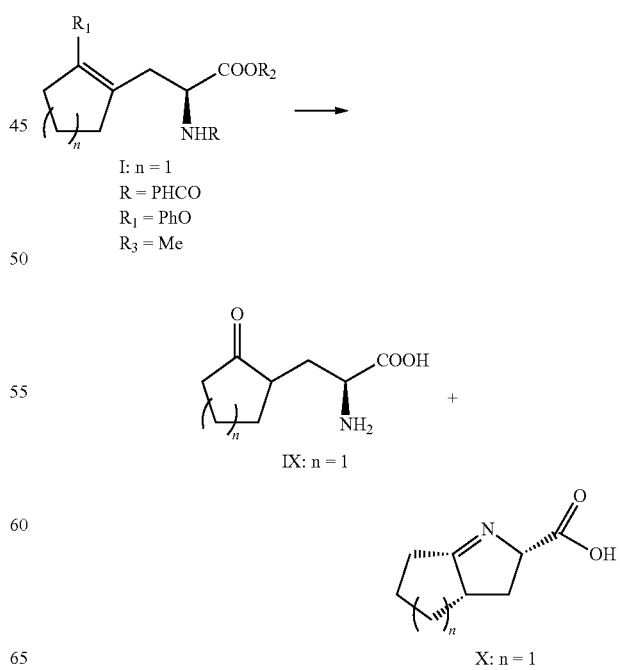

I: n = 1
R = PHCO
R$_1$ = PhO
R$_3$ = Me

IX: n = 1

X: n = 1

To 60 g of the oil product obtained in example 5, 170 mL of 6 N HCl was added, and the mixture was refluxed overnight. After cooling to room temperature, the mixture was extracted with MTBE (2×50 mL) twice. The aqueous layer was concentrated under reduced pressure to dryness to provide gray solid as a mixture of IX and X as their hydrochloric acid salts which was used directly for next step without further purification.

Example 10

Hydrolysis of (IA) into (2S)-methyl 2-benzamido-3-(2-oxocyclopentyl)propanoate (IX)

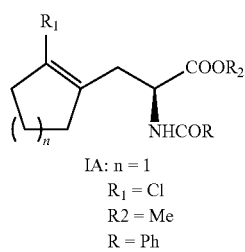

IA: n = 1
R$_1$ = Cl
R$_2$ = Me
R = Ph

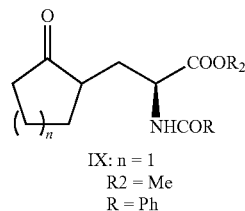

IX: n = 1
R$_2$ = Me
R = Ph

To a mixture of concentrated sulfuric acid (162.8 g) and dichloromethane (185 mL) was added a solution of 61.4 g of IA (n=1, R$_1$=Cl, R$_2$=Me, R=Ph) in dichloromethane (105 mL) at −5~0° C. and stirred for another 30 min while maintaining this temperature. Then the cooling bath was removed and the mixture was stirred at 8-13° C. for additional 2-3 h. When the reaction was completed, the reaction mixture was poured into 400 mL of cooled water. The aqueous phase was extracted with 100 mL of dichloromethane. The combined organics were washed with brine twice and concentrated. Thus obtained crude material was used directly in the next step. To obtain pure analytical sample, the crude material was dissolved in 480 mL of MTBE, and were added 30 g of sodium sulfate and 5 g active charcoal. The mixture was then refluxed for 30 min and then filtered when the mixture cooled to around 35° C. Removal of c.a. 300 mL of MTBE and then to the solution was added 400 mL of heptane to afford yellow solid 42 g in 65% yield.

$^1$H NMR (CDCl$_3$, δ): 7.90-7.85 (m, 2H), 7.80 (br, 1H), 7.52-7.26 (m, 3H), 4.87-4.72 (m, 1H), 3.77 (s, 3H), 2.51-1.90 (m, 7H), 1.90-1.60 (m, 2H).

Example 11

Hydrolysis of (IX) (n=1, R2=Me, R=Ph) into a mixture of (2S)-2-amino-3-(2-oxocyclopentyl)propanoic acid (IX) and (2S)-2,3,3a,4,5,6-hexahydrocyclopenta[b]pyrrole-2-carboxylic acid (X)

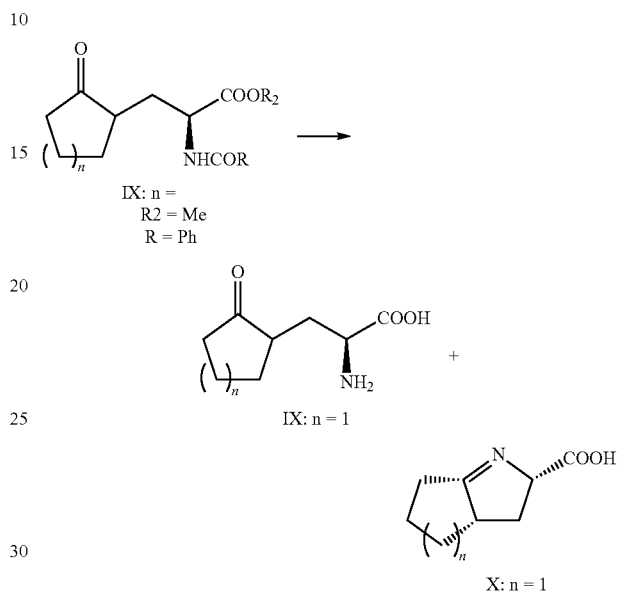

To 42 g of the solid product obtained in example 10, 130 mL of 6 N HCl was added, and the mixture was refluxed overnight. After cooling to room temperature, the mixture was extracted with MTBE (2×30 mL) twice. The aqueous layer was concentrated under reduced pressure to dryness to provide gray solid as a mixture of IX and X as their hydrochloric acid salts which was used directly for next step without further purification.

Example 12

Preparation of (2S,3aS,6aS)-octahydrocyclopenta[b]pyrrole-2-carboxylic acid(II)

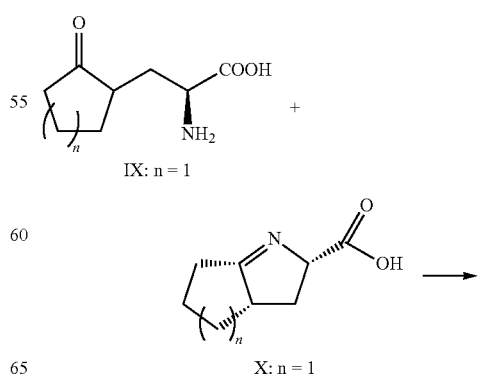

-continued

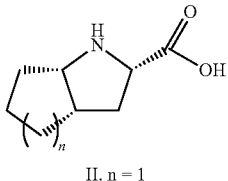

II. n = 1

To a residue (2.3 g) obtained in example 6 was added 20 mL of water. The pH was adjusted to 1 to 2 using hydrochloric acid and then the solution was charged into an autoclave. 100 mg of 10% palladium/carbon was also charged into the autoclave. Then the reactor was charged with hydrogen to 10 bar and heated at 80° C. overnight until hydrogen take up ceased. The system was cooled and hydrogen was released carefully. The catalyst was removed by filtration and the filtrate was concentrated under reduced pressure. The residue was treated with 1 ml water and 10 ml acetone and cooled to −15° C. to afford the desired compound as its hydrochloric acid salt.

$^1$H NMR (D$_2$O, δ): 4.22 (m, 1H), 4.11 (m, 1H), 2.91 (m, 1H), 2.56 (m, 1H), 1.91-1.48 (m, 7H).

While the invention has been disclosed in connection with the preferred embodiments and methods of use, it is to be understood that many alternatives, modifications, and variations thereof are possible without departing from the present invention. Thus, the present invention is intended to embrace all such alternatives, modifications, and variations as may be apparent to those skilled in the art and encompassed within the hereinafter appended claims.

What we claim:

1. A process for preparing an enantiomerically enriched cycloalkylene-substituted alanine compound having the structure:

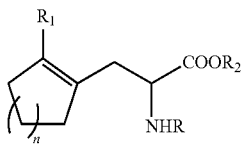

Formula (I)

comprising the step of asymmetrically hydrogenating a dehydro amino acid compound having the structure:

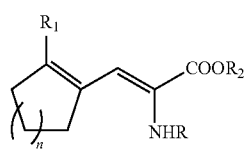

Formula (V)

in a suitable reaction media in the presence of a catalyst having a transition metal moiety complexed to a chiral phosphine ligand wherein:
  n is 1, 2, 3, or 4,
  R is selected from the group consisting of hydrogen, alkyl, aryl and —COR$_4$, R$_1$ is selected from the group consisting of hydrogen, halogen, alkyl, aryl, alkoxy, aryloxy and —COOR$_4$, and R$_2$ is selected from the group consisting of hydrogen, alkyl and aryl groups, wherein each R$_4$ is independently selected from the group consisting of alkyl and aryl groups;

to prepare enantiomerically enriched cycloalkyene substituted alanine compounds having the structure of Formula (IA) or (IB):

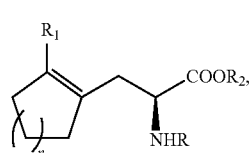

Formula (IA)

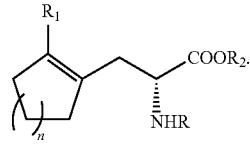

Formula (IB)

2. The process of claim 1, wherein the chiral phosphine ligand catalyst having the formula M(L)(P*)X, wherein:
  M is selected from the group consisting of Rh, Ru, and Ir or a salt or a complex thereof;
  L is 1,5-cyclooctandiene or 2,5-norbornadiene;
  P* is a chiral phosphine compound,
  and X is an anion.

3. The process of claim 2, wherein P* is a compound selected from the group consisting of ScRp-DuanPhos, RcSp-DuanPhos, SSRR-TangPhos, BINAP, DuPhos and BPE.

4. The process of claim 3, wherein X is a tetrahaloborate.

5. The process of claim 4, wherein the catalyst is [Rh(COD)(ScRp-DuanPhos)]BF$_4$ or [Rh(COD)(RcSp-DuanPhos)]BF$_4$.

6. The process of claim 1, wherein said dehydro amino acid compound of Formula V is prepared by a process comprising the step of converting an unsaturated aldehyde having the structure:

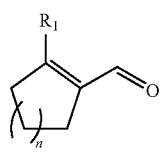

Formula (VI)

to an azlactone compound having the structure:

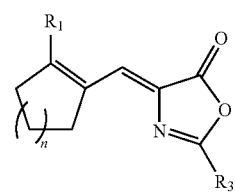

Formula (VIII)

wherein:
  n=1, 2, 3 or 4;
  R$_1$ is selected from the group consisting of hydrogen, chloro, bromo, phenoxy, alkoxy and naphthoxy, and R$_3$ is alkyl or aryl,
wherein the conversion of azlactone compound of Formula (VIII) to a prochiral dehydro amino acid of Formula (V) is accomplished by alcoholysis.

7. The process of claim 6, wherein said conversion of unsaturated aldehyde to azlactone occurs under Erlenmeyer reaction conditions.

8. The process of the claim 7, wherein $R_2$ is hydrogen, methyl or ethyl.

9. The process of claim 1, wherein the asymmetric hydrogenation is accomplished at the presence of [Rh(COD)(ScRp-DuanPhos)]$BF_4$ or [Rh(COD)(RcSp-DuanPhos)]$BF_4$.

10. The process of claim 1, wherein the compound of Formula (Ia) or Formula (Ib) further undergo a hydrolysis step to prepare a compound having a structure of Formula (IX), Formula (X) or a mixture thereof:

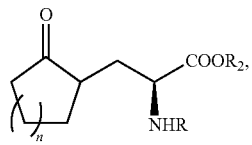

Formula (IX)

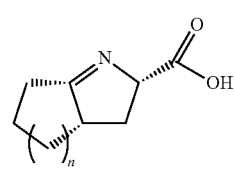

Formula (X)

n is 1, 2, 3, or 4, and

R and $R_2$ are independently selected from the group consisting of hydrogen, halogen, alkyl and aryl.

11. The process of claim 10, further comprising a step of preparing a cyclic amino acid compound having the structure of Formula II:

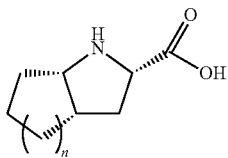

Formula (II)

by catalytically hydrogenating the compounds of Formula (X), wherein n is 1, 2, 3, or 4.

12. The process of claim 11, wherein said catalytic hydrogenation comprises a metal-based hetero or homo catalyst selected from the group consisting of Pt, Pd, Ru, Rh and Ir with or without a ligand.

13. The process of claim 1, wherein the reaction media is selected from a group consisting of dichloromethane, methanol, tetrahydrofuran, toluene, ethyl acetate, and combinations thereof.

14. The process of claim 13, wherein the temperature during the reaction ranges from about 10 to about 50° C.

15. The process of claim 1, wherein the hydrogen pressure during the reaction ranges from about 1 to about 50 bar.

16. A compound having a structure:

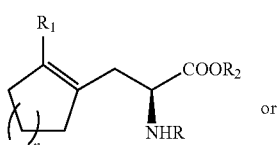

Formula (IA)

or

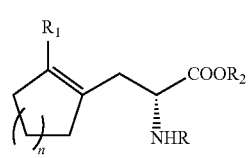

Formula (IB)

wherein n is 1, 2, 3, or 4,

R is selected from the group consisting of hydrogen, alkyl and —$COR_4$, $R_1$ is selected from the group consisting of halogen, alkyl, alkoxy, aryloxy and $COR_4$, $R_2$ is selected from the group consisting of hydrogen, and alkyl, and each $R_4$ when present is independently selected from the group consisting of alkyl and aryl groups.

17. The compound of claim 16, wherein and $R_1$ is a halogen, an alkoxy or an aryloxy.

18. The compound of claim 16, wherein the alkoxy is selected from the group consisting of methoxy, ethoxy, propoxy, and t-butoxy.

19. The compound of claim 16, wherein the aryloxy is phenoxy.

20. The compound of claim 16, wherein the halogen is chlorine.

21. The compound of claim 16, wherein $R_2$ is a methyl or an ethyl.

22. The compound of claim 16, wherein n is 1.

* * * * *